United States Patent [19]

Underwood

[11] Patent Number: 4,654,026

[45] Date of Patent: Mar. 31, 1987

[54] INTRAVASCULAR TUBE ASSEMBLY

[76] Inventor: Mara Z. Underwood, 180 Upper Gulph Rd., Radnor, Pa. 19087

[21] Appl. No.: 686,287

[22] Filed: Dec. 26, 1984

[51] Int. Cl.$^4$ .............................................. A61M 5/00
[52] U.S. Cl. ..................................... 604/80; 604/173; 128/DIG. 26; 138/112
[58] Field of Search .............................. 24/345, 30.55; 604/80–86, 56, 92, 173, 246–262, 408–410; 128/DIG. 26; 138/108, 112

[56] References Cited

U.S. PATENT DOCUMENTS

| | | | |
|---|---|---|---|
| 2,690,181 | 9/1954 | Boyer | 604/275 X |
| 2,896,619 | 7/1959 | Bellamy | 604/262 X |
| 2,954,028 | 9/1960 | Smith | 604/80 |
| 3,316,935 | 5/1967 | Kaiser et al. | 604/250 X |
| 3,696,920 | 10/1972 | Lahay | 128/DIG. 26 |
| 4,072,146 | 2/1978 | Howes | 128/674 |
| 4,150,673 | 4/1979 | Watt | 604/110 X |
| 4,219,021 | 8/1980 | Fink | 604/248 |

FOREIGN PATENT DOCUMENTS 2021418 12/1979 United Kingdom .

Primary Examiner—Dalton L. Truluck
Attorney, Agent, or Firm—Gerry J. Elman

[57] ABSTRACT

An intravascular tube assembly is disclosed which facilitates the administration of drugs and fluids to a patient. The invention is especially useful during emergency surgery, or in other contexts where several medications need to be administered simultaneously, and wherein it is necessary to provide a complicated assortment of infusion lines. The assembly comprises a plurality of tubes for delivering the fluids, the tubes having indicia disposed at intervals along their length. In the preferred embodiment, the indicia are printed on the tubes at intervals of about six inches, and are printed three times at each location along the tube, around its circumference. Alternatively, the indicia can be printed in a spiral fashion from one end of the tube to the other. The assembly also includes at least one generally flat separator having a plurality of spaced-apart holes, the diameter of the holes being slightly larger than the diameter of the tubes. The separator has slots which permit the tubes to be quickly snapped into place. The separator therefore maintains the tubes in spaced relation, and prevents them from becoming tangled during the operation. The indicia on each tube are unique to that tube, inabling operating room personnel quickly to inject the proper fluid into the patient, without the need to trace the path of the tube from its fluid source.

21 Claims, 10 Drawing Figures

INTRAVASCULAR TUBE ASSEMBLY

BACKGROUND OF THE INVENTION

This invention relates to the field of emergency room medicine, including the care of a patient during surgery, as well as during intensive care. The invention comprises a novel assembly of intravascular tubes which facilitates the rapid and safe injection of intravascular fluids into a patient. By "intravascular" it is meant that the injections described herein may be either intravenous or intra-arterial. That is, the present invention can be used to inject fluids into both veins and arteries.

For example, when a patient is admitted to a hospital for emergency surgery, it is usually necessary to administer multiple intravascular fluids, including various drugs or blood. Also it may be necessary to sample the patient's blood, and to measure the patient's blood pressure at different points. Because of adverse drug interactions, it is necessary to prevent the various drugs and fluids from being mixed before entering the bloodstream. Also, there is usually a need to administer multiple intravenous infusions rapidly. Thus, it is common to employ a plurality of separate tubes for each substance being administered to, or withdrawn from, the patient.

In an emergency room, operating room, or intensive care unit, this multiplicity of tubes can be hazardous. The correct medication must be administered promptly at the correct site. But the greater the number of tubes, the greater the likelihood that the tubes will become tangled. Entanglement of the tubes, at worst, can cause fatal errors in administering drugs and fluids. At best, such entanglement slows the operation, due to the extra time required to guard against error by tracing the path of each tube. Although the time required to trace the path of a tube may not seem long in absolute terms, even a short delay in administering a necessary fluid can be too long during emergency surgery. During such surgery, there is little or no time to think, especially when the life of the patient is threatened, and when so many drugs need to be given quickly and during a short period of time.

Even after the operation is concluded, it is necessary to keep the various intravascular tubes separated and organized. After a typical operation, the patient is often left with an entanglement of intravascular tubes placed on or near the chest. In order to facilitate transport of the patient following the operation, it is important that such tubes not become tangled at sites near the body. Then, after transport to the intensive care unit or the recovery room, there begins the usually frustrating task of untangling and separating the tubes while, hopefully, not dislodging them in the process. Not only is this scenario time-consuming, but it is actually dangerous, especially if the patient requires intravenous medication immediately after transport.

There are many examples of intravascular tube assemblies in the prior art. For example, U.S. Pat. No. 3,316,935 a plurality of flexible tubes for use in administering fluids to a patient. Another example of an assembly of tubes for similar purposes is shown in U.S. Pat. No. 2,954,028. U.S. Pat. No. 4,308,642 gives an example of a structure for supporting an intravascular tube alongside a hospital bed.

The prior art discloses the use of intravascular tube assemblies, and some, such as the first two patents cited above, disclose types of separator means for holding the tubes in spaced relation. The present invention, however, provides a safe and inexpensive means to prevent entanglement of the intravascular tubes, as well as as a means for identifying the tubes rapidly and reliably when time is of the essence. This invention is particularly suited not only to situations where one needs to administer many fluids to a patient, but also to cases where one does not know, beforehand, how long the patient will need each such fluid.

SUMMARY OF THE INVENTION

The present invention solves the problems described above by a plurality of intravascular tubes, each bearing unique indicia. The indicia, which may be numbers, letters, bands of color, or the like, are printed along the length of each tube at constant intervals, preferably of about six inches. At each location along the length of the tube, the indicia are repeated two or three times, around the circumference of the tube. Alternatively, the indicia are printed once at each location, in a spiralling pattern along the tube, so that in one quick glance a single tube can be identified in its entirety.

The tubes are adapted, at one end, to be connected to a source of intravascular fluid, and are similarly adapted, at the other end, to be connected to a cannula or other means for injecting fluid into a patient. The indicia appearing along a given tube also appear on the collecting chamber for intravascular fluid, from which the tube receives its fluid, as well as on the plastic insert at the other end of the tube which is attached to a cannula. If the tube is to be used with other devices, besides the cannulae and fluid bags, then such other devices should be marked with indicia corresponding to the indicia of the attached tube.

The invention also includes at least one separator having a plurality of spaced-apart holes. In the preferred embodiment, the separator is constructed of a flat piece of plastic, and the holes are generally key-shaped, so as to permit the tubes to be snapped into and out of the separator. There are no indicia on the separator; any given tube may be inserted into any available hole in the separator.

In an alternative embodiment, the separator has at least one groove, into which the tube may be inserted, and such that the tube may be wound around the portion of the separator defining the groove. This embodiment therefore permits excess tubing to be wound up, and eliminates the confusion caused by the presence of unnecessarily long lengths of tubing.

It is therefore an object of the invention to provide an intravascular tube assembly which facilitates the progress of emergency room procedures, surgical operations, anesthesia, and intensive care.

It is a further object of the invention to provide an assembly as described above, wherein the assembly includes means tending to prevent the entanglement of the intravascular tubes during an operation, or during the course of other care of a patient.

It is a further object of the invention to provide an assembly as described above, wherein each tube of the assembly may be rapidly and reliably identified, without the need to trace the path of the tube.

It is a further object of the invention to provide an assembly as described above, wherein different groups of tubes may be held in spaced relation by different separators.

It is a further object of the invention to provide an assembly which maximizes the ability of operating room or intensive care personnel to administer as many fluids and/or medications as are necessary for the patient, and which minimizes the time required to administer such fluids.

It is a further object of the invention to provide a kit which can be used to construct an intravascular tube assembly for use in emergencies, surgical procedures, and administration of anesthesia, and in intensive care units.

It is a further object of the invention to provide a method of treating a patient in an emergency situation, which method minimizes the time spent in attending to mechanical difficulties and in the identification of numerous intravenous tubings, and which maximizes the time available for delivering a plurality of vital fluids to the patient.

Other objects and advantages of the invention will be apparent to those skilled in the art, from a reading of the following brief description of the drawings, the detailed description of the invention, and the appended claims.

DETAILED DESCRIPTION OF THE INVENTION

The present invention comprises an assembly of intravascular tubes, which can be used to treat a patient quickly and safely during an emergency, during surgery, or in an intensive care unit. The invention is especially helpful in reducing the time required to locate and administer the proper intravascular fluid. However, the assembly disclosed herein may also be used in non-emergency situations, whenever a plurality of fluids must be injected and/or withdrawn from the patient.

Figure 1:
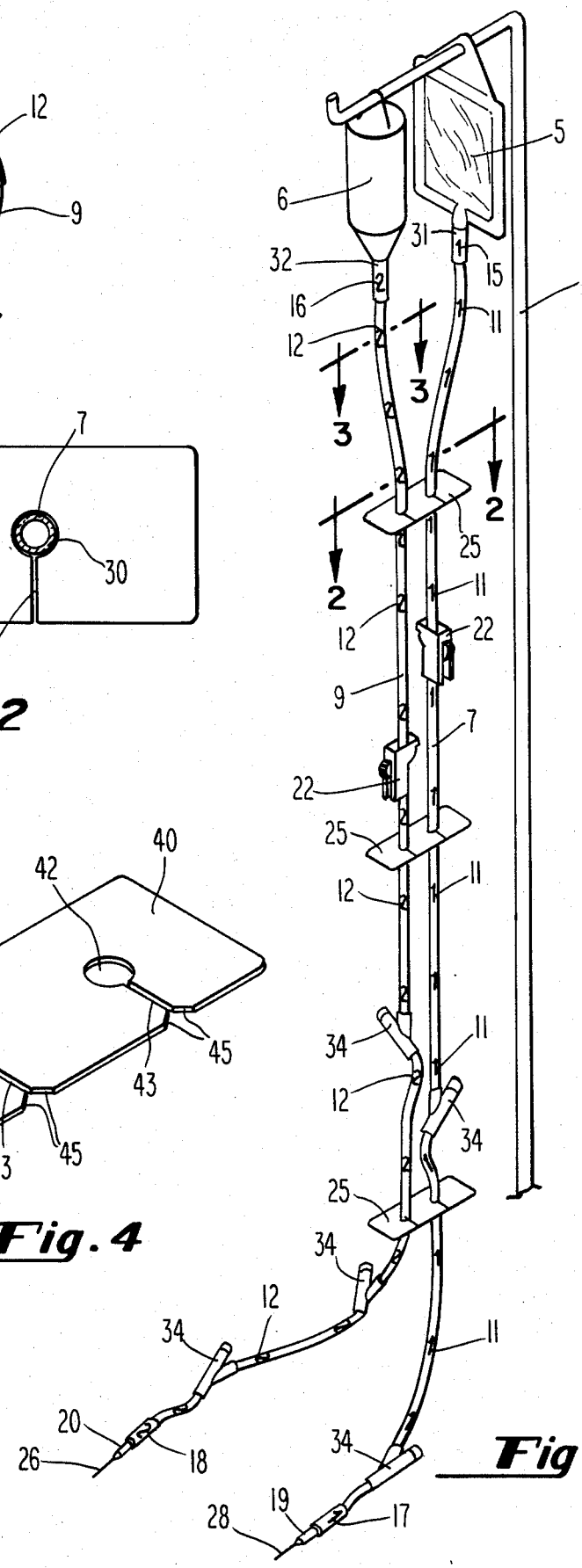
FIG. 1 is a perspective view showing a pair of tubes, constructed according to the present invention, suspended from an overhead rack.

FIG. 1 is a perspective view of one embodiment of the invention. Intravascular tubes 7 and 9 are attached to fluid bags 5 and 6, respectively. Fluid bags 5 and 6 are suspended from overhead rack 1 which may be conveniently mounted alongside the bed of a patient (not shown). In practice, there may be 2—4 such racks, although usually all bottles and fluid sources are suspended from the same rack. Tubes 7 and 9 are preferably constructed of clear plastic, so that the color of the fluid flowing therethrough may be easily identified. The tubes have flow regulators 22 disposed thereon, for stopping the flow of fluid through the tubes when necessary. The number of flow regulators is not critical, and can be varied at will. The tubes are preferably identical in diameter. However, the lengths of the tubes may be different, to suit different operating room configurations.

Disposed at intervals along the tubes 7 and 9 are indicia, designated generally by reference numerals 11 and 12. In the embodiment depicted in FIG. 1, the indicia comprise numbers printed on the tubes. However, the indicia can assume other forms. For example, letters, bands of color, or other symbols may be used. The indicia could even comprise simple mnemonic codes identifying certain drugs which are most commonly required during an emergency or during surgery. What is important is that the same symbol be used along the same tube, and that no tube bear indicia identical to those of any other tube.

In the preferred embodiment, the indicia are disposed along the tube at intervals of about six inches, but other spacings are feasible. It is desirable that the intervals be reasonably short, so that each tube, if inspected at any point along its length, can be readily identified.

Fluid bags 5 and 6 are connected to tube adapters 31 and 32, respectively, and the adapters also bear indicia 15 and 16. Indicia 15 and 16 are the same as indicia 11 and 12, respectively, on the attached tubes. It is important that the indicia on the adapter match the indicia on the attached tube, so that the indicia on the tube can identify the fluid flowing therethrough. The other ends of tubes 7 and 9 are connected to cannulae 28 and 26 by cannula connectors 19 and 20. The cannula connectors 19 and 20 bear indicia 17 and 18, which are also the same as indicia 11 and 12, respectively, for the same reasons.

Tubes 7 and 9 are also provided with a plurality of injection portals 34, which allow the injection of various fluids and medications at different locations along the tubes. Also, additional intravascular tubes, from other sources, can be inserted into the injection portals in a "piggyback" fashion. Thus, the tubes shown in the figure can also be used to deliver supplemental fluids or medications, besides those which come from bags 5 and 6.

It is understood that the tubes may be provided with an assortment of components, in addition to the injection portals, such as filters, one-way valves, micro-drippers, macro-drippers, and clamps. These additional items are not shown in FIG. 1, for the sake of clarity.

Figure 2:
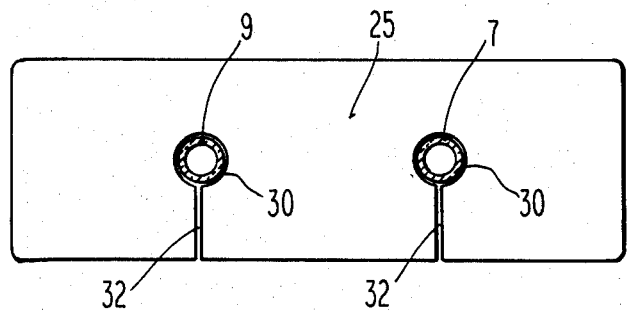
FIG. 2 is a view taken along the line 2—2 of FIG. 1, showing a top view of one of the separators, and showing the tubes in cross-section.

Tubes 7 and 9 pass through separators 25 which are visible in FIG. 1. FIG. 2, being taken along the line 2—2 of FIG. 1, provides a top view of separator 25, and includes cross-sectional views of tubes 7 and 9. Separators 25 define holes 30, which are connected with the periphery of the separators by slots 32. Separators 25 are preferably constructed of plastic. Plastic construction is preferred, partly to minimize the weight of the assembly, and partly to permit the slots 32 to be opened momentarily to allow the intravascular tubes to be snapped in. The diameter of the holes is slightly larger than the diameter of the tubes, so as to allow the tubes to slide easily relative to the separator.

Figure 3:
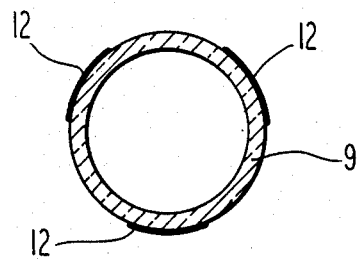
FIG. 3 is a cross-sectional view of one of the intravascular tubes of the present invention, taken along the line 3—3 of FIG. 1, and illustrating the indicia disposed on the tube.

The indicia imprinted on the tubes are preferably imprinted more than once at each location along the tubes. FIG. 3, which shows tube 9 in cross-section, illustrates indicia 12 disposed around the circumference of the tube. The indicia appear at intervals of 120°.

Other configurations are possible; for example it is possible to provide four sets of indicia at each location, spaced at intervals of 90° even two sets, spaced at intervals of 180°. It is desirable that the indicia be repeated more than twice, around the tube circumference, so that the tube may be quickly identified regardless of its orientation relative to the observer.

In still another alternative arrangement, the indicia can be printed in a spiral fashion along the tubes. That is, the indicia appear only once at each location, but at each successive location, which can be about four inches away, the indicia are rotated around the tube by 90°. Thus, one can identify the fluid or medication in the tube by glancing quickly at the length of tubing and by immediately observing its indicia.

As stated above, the indicia appearing on each tube must also appear on the fluid bag, cannula, or any other device that is attached to the ends of the tube. However, the separators 25 must not bear any indicia. Any tube may be used in any hole of any separator. It is important, in the limited time available during an emergency, that the tubes be quickly snapped into the first available hole of a separator. It is the indicia on the tube, and the matching indicia on the connected input and output devices, which identify the tube. The separators serve no similar identifying function, but only act to organize spatially related tubing to prevent entanglement.

Figure 4:
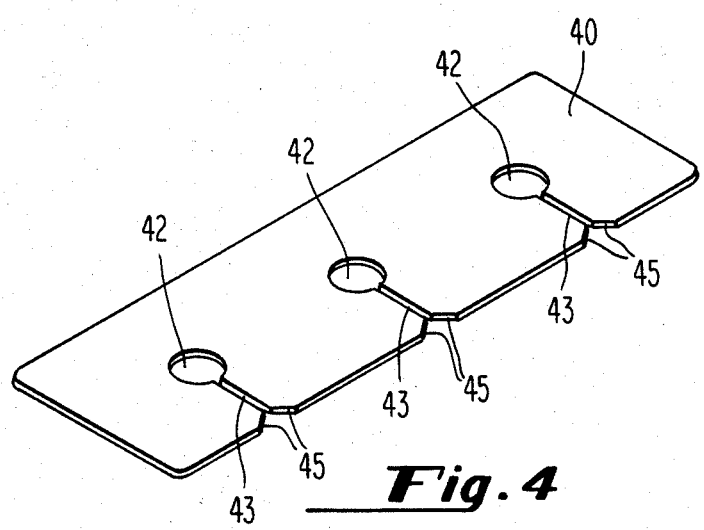
FIG. 4 is a perspective view of one of the separators adapted for holding the intravascular tubes in spaced relation.

FIG. 1 shows only two intravascular tubes, for clarity of illustration. It is understood, however, that the invention may be practiced with additional tubes. FIG. 4 shows, in perspective, another separator 40, similar to separators 25, which accommodates three tubes at once. Separator 40 includes holes 42 and slots 43, and is otherwise similar in construction to separator 25 of FIG. 2.

The separator of FIG. 4 is also provided with notches 45. This is an alternative construction to that of FIG. 2, and permits the tubes to be inserted into the separator more easily.

Figure 6:
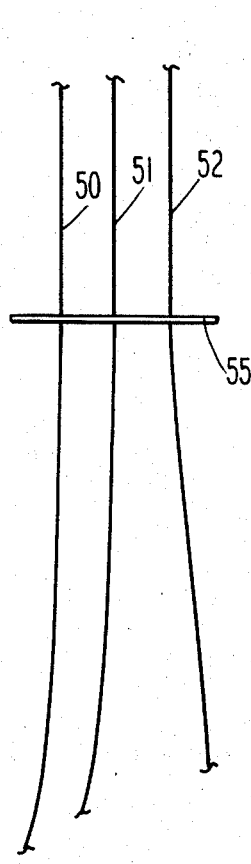
FIGS. 6, 7, and 8 are schematic diagrams showing alternative arrangements of tubes and separators, according to the present invention.
Figure 7:
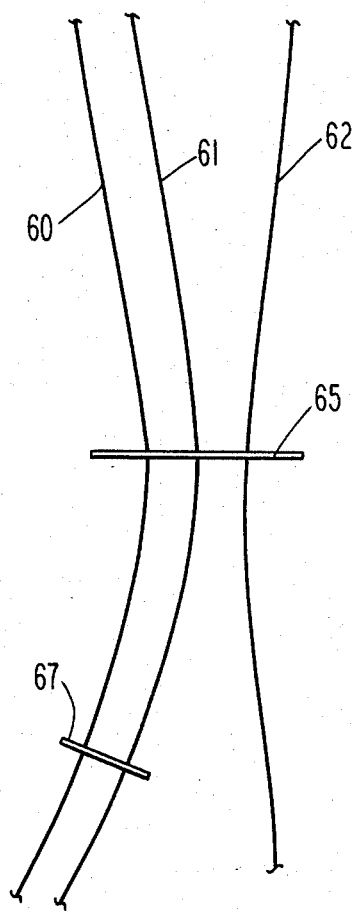
Figure 8:
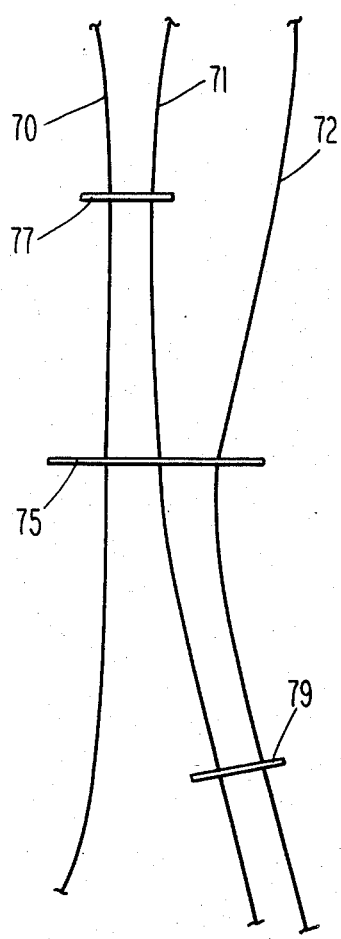

In FIG. 1, there are three separators 25, each having two holes. If three or more tubes are used, and if groups of tubes need to be directed to different sites on the patient's body, then other combinations and sizes of separators may be employed. FIGS. 6, 7, and 8 illustrate, in schematic form, several of such alternative arrangements.

FIG. 6 illustrates one simple arrangement involving three intravascular tubes 50, 51, and 52, all passing through one separator 55. The separator 55, like all of the separators illustrated schematically in FIGS. 6–8, is similar to the separators shown in FIGS. 2 and 4.

FIG. 7 illustrates an arrangement in which all three tubes 60, 61, and 62 pass through holes in separator 65, but wherein only tubes 60 and 61 pass through holes in separator 67.

FIG. 8 illustrates an arrangement wherein all three tubes 70, 71, and 72 pass through holes in separator 75. Only tubes 70 and 71 pass through holes in separator 77, and only tubes 71 and 72 pass through holes in separator 79.

Figure 5:
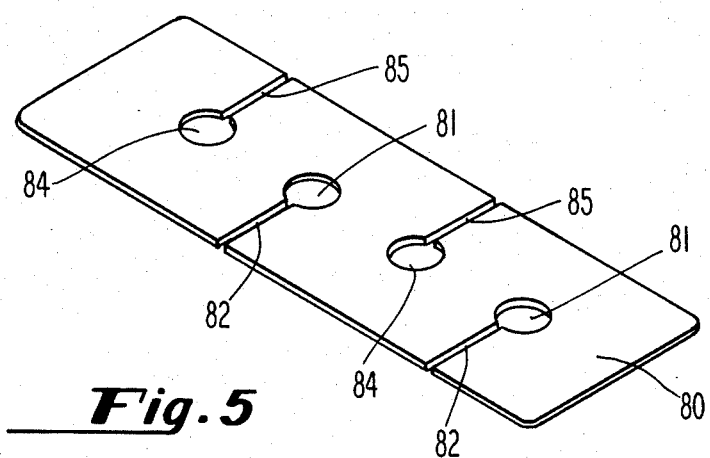
FIG. 5 is a perspective view of an alternative embodiment of a separator made according to the present invention.

FIG. 5 illustrates another embodiment of the separators. Separator 80 includes four holes and four slots. Holes 81 communicate with slots 82, and holes 84 communicate with slots 85. Slots 82 and 85 are disposed on opposite sides of separator 80. Thus, in using the separator 80, some tubes are snapped in on one side of the separator, and other tubes are snapped in on the other side.

Figure 9:
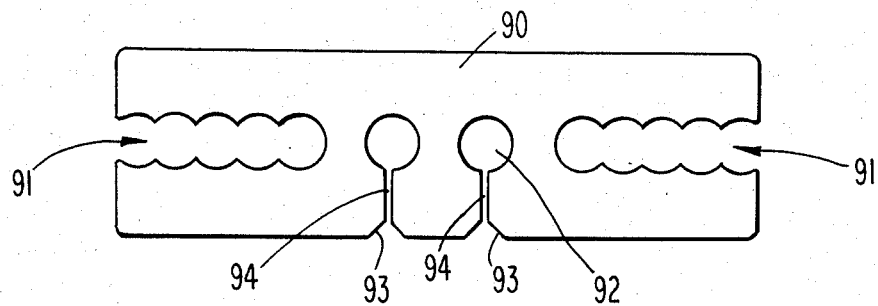
FIG. 9 is a plan view of a separator constructed according to an alternative embodiment of the invention.

FIG. 9 is a plan view of a separator constructed according to an alternative embodiment. Separator 90 defines grooves 91, preferably disposed on both sides of the separator. The separator also has holes 92, slots 94, and notches 93, similar to those of the separator described above. The grooves 91 allow excess tubing to be wrapped around the separator, and to be kept out of the way of the physician.

Figure 10:
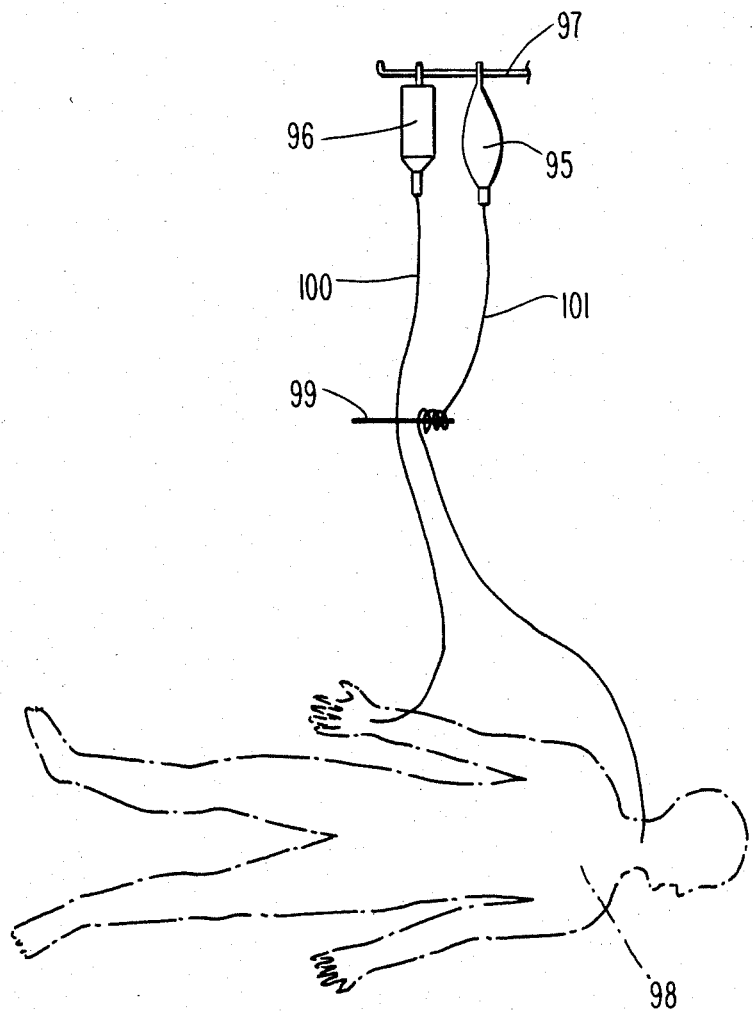
FIG. 10 is a partially schematic view illustrating the use of the embodiment of FIG. 9, in the treatment of a patient.

FIG. 10 illustrates the use of the separator shown in FIG. 9. Patient 98 is shown receiving infusions of fluids or medications from fluid containers 96 and 95, which containers are suspended from rack 97. Tubes 100 and 101 extend from containers 96 and 95, respectively, and pass through separator 99. Separator 99 is constructed in a manner similar to that of separator 90 of FIG. 9. Both tube 100 and tube 101 pass through holes (not visible in FIG. 10) of separator 99. Tube 101 is also wound around the portion of the separator defined by the groove, so that there is virtually no excess tubing hanging in the vicinity of the patient. The tubing that is so wrapped around the separator can later be unwound, if the overall length of the tubing needs to be increased.

It will be appreciated that the embodiment illustrated in FIGS. 9 and 10 is a vast improvement over techniques of the prior art. In the past, it has been common for nurses to wrap excess lengths of tubing around their hands, and then to tape the resulting roll of tubing in place. With the present invention, the same goal can be accomplished more easily and more reliably. The embodiment described is especially useful during transport of the patient, when it is important not to have long lengths of tubing hanging down from the patient. After the patient has been moved to a recovery room, or intensive care unit, the tubing can be unwound if necessary.

Clearly, other shapes for the separators are possible. The separators may be square, or even polygonal or curved. Also, the number of slots and holes may be increased, as permitted by the surface area of the separators, to accommodate additional tubes.

The operation of the invention may be summarized as follows. When a patient is admitted to an emergency operating room, a plurality of fluid containers holding the substances deemed necessary by the physician in charge are connected to tubes having corresponding indicia. It is, of course, crucial that the indicia on a given tube match the indicia on the fluid container to which the tube is attached. A plurality of cannulae are inserted into various areas of the body which areas are not readily identified when looking at the plurality of tubes located near the patient's head. These cannulae are attached to the other ends of the tubes, again with attention being given to the matching of indicia on the tubes and the syringes.

When the patient needs an infusion of a given fluid or medication, the physician quickly notes the indicia on the container storing a particular fluid, or on an injection portal on a particular IV tube. The physician can immediately identify what type of line this is (e.g. an arterial line, or a central venous line, etc.), and to which body area it is going. This identification is important since various medications should never given intraarterially, while others should only be given into venous access line. While attempting to administer the fluid or medication, the physician may also be guided by the presence of similar indicia appearing on the lower ends of the tubes, near the areas of the body at which the fluids are ultimately being received. It is an important advantage of the invention that, after the tubes have been connected to properly labeled fluid bags and cannulae, or the like, it is no longer necessary to trace the path of a tube, regardless of how tangled the tubes have become.

One or more separators can also be snapped onto the tubes to reduce further the likelihood of entanglement and confusion of the tubes. As shown above, groups of tubes can be channeled to different areas on the patient's body by using a plurality of separators, the separators engaging different tubes, in a manner suggested by FIGS. 6–8.

When additional medication is needed, the correct tube may be identified simply by reference to its indicia, or by reference to the matching indicia on the fluid source or syringe. One first observes the indicia on an intravenous or intra-arterial cannula inserted into the patient, and then replaces the fluid bag with another (having the same indicia) at the other end of the tube (which also bears the same indicia. The other end of the tube is located simply and quickly by identifying its indicia. Indeed, one may start at either end (or the middle) of a given tube, and quickly locate the other end, without tracing its path.

It is noteworthy that there is no need to label the intravascular tubes after the operation is concluded, since the tubes are clearly labeled before they are used. This feature further distinguishes the present invention from the prior art, wherein it has been customary for nurses to affix labels to the tubes after the operation, when the emergency is over.

The present invention not only improves the efficiency of emergency treatment, but it also reduces the amount of post-operative effort required. Because the intravascular tubes have been properly organized from the beginning, there is no need to perform the organizing task later. The invention thus provides financial savings for hospitals, both by reducing the labor required of hospital employees, and by decreasing the overall turnover time for operating rooms.

The present invention may also take the form of a kit which can be used to organize the procedures of an operating room. The kit, in its preferred form, comprises at least two tubes, the tubes bearing indicia as described above, the indicia on one of the tubes being different from the indicia on any of the other tubes, and a set of separators by which the tubes may be held in spaced-apart relation. It is possible to include, in the kit, extra tubing having the same or other indicia, but it is preferable that no two tubes, within the same kit, bear the same indicia. Thus, one reduces the risk that two tubes bearing the same indicia will accidentally be used during an operation.

The kit as presented will contain an adapter for connection of one end of the tube to a fluid bag, the adapter having indicia matching the indicia on one of the tubes, and a cannula connector, also bearing unique indicia, for connecting the other end of the tube to a cannula, with the adapter, tubing and connector being a single unit. Clearly, the type and number of the tubes, separators, and adapters can be varied considerably, within the scope of the invention.

It is apparent that the objects of the invention are fulfilled by the above disclosure. It is understood, however, that many modifications may be made to the basic invention. The number and shape of the separators, the types and distribution of the indicia, and the kinds of flow regulators and auxiliary equipment can all be varied, as indicated above. The contents of a particular kit made according to the invention can be modified to suit particular surgical needs. The tubes may be provided with varying numbers of additional components, such as injection portals, clamps, and other devices. These and other such modifications are to be deemed within the spirit and scope of the following claims.

What is claimed is:

1. An intravascular tube assembly, comprising:
   (a) at least two substantially clear, plastic intravascular tubes, each of the tubes being connected at one end, to
   (b) a tube adapter, each of said tube adapters being adapted to sealably connect a source of fluid to be injected into a patient to one of the tubes,
   (c) each of the tubes being connected at the other end to a cannula connector,
   (d) each of said cannula connectors being adapted to sealably connect one of the tubes with means for injecting fluids into the patient,
   (e) the tubes having a plurality of indicia displayed along each of said tubes at predetermined intervals, the indicia appearing on a given tube being different from the indicia appearing on any other tube of the assembly, the indicia appearing on one of said tubes being the same along the length of that tube, and
   (f) at least one generally flat separator, the separator having a plurality of spaced-apart holes, the holes being adapted to receive said tubes, wherein the separator maintains the spacing of the tubes passing therethrough, and wherein the separator has at least one slot connecting the separator hole with the edge of the separator, whereby one of the tubes may be quickly placed within or removed from the separator hole.

2. The assembly of claim 1, wherein the indicia are displayed at least twice at each location along the tube, around the circumference the tube.

3. The assembly of claim 1, wherein the indicia are displayed times at each location along the tube, around the circumference the tube.

4. The assembly of claim 2, wherein there are at least three tubes and at least three separators, and wherein the separators comprise means for directing groups of said tubes to different locations.

5. The assembly of claim 2, wherein the separator includes slots communicating with the holes, the slots having notched ends.

6. The assembly of claim 2, wherein the tubes include at least one injection portal for injecting fluid into the tubes.

7. The assembly of claim 2, wherein the separator has a plurality of slots, all disposed along the same side of the separator.

8. The assembly of claim 2, wherein the separator has a plurality of slots, alternate slots being disposed on opposite sides of the separator.

9. The assembly of claim 2, wherein the separator defines at least one groove, the groove being sufficiently wide to permit the wrapping of a length of tubing around the portion of the separator defining the groove.

10. An intravascular tube assembly comprising:
    (a) a support means,
    (b) at least two means for storing fluids, the storage means being suspended from the support means, each of the storage means being connected to indicia-bearing adapter means for connecting a tube to the storage means, (c) at least two substantially clear, plastic intravascular tubes, each tube being connected at one end to the respective adapter means of the respective storage means, each tube having a plurality of indicia disposed at substantially constant intervals along the length of the tube, the indicia displayed on any one of the tubes being different from the indicia on any of the other tubes, (d) indicia-bearing cannula connector means, attached to the other ends of the tubes, and (e) at least two separators, the separators comprising generally flat members having spaced-apart holes through which the tubes are received, the holes being adapted to receive said tubes, wherein the separator maintains the spacinq of the tubes passing therethrough, and wherein the separator has at least one slot connecting the separator hole with the edge of the separator, whereby one of the tubes may be quickly placed within or removed from the separator hole, (f) wherein the indicia on each tube match the indicia on the adapter means and the cannula connector means to which the tube is connected.

11. The assembly of claim 10, wherein the indicia on the tubes are displayed at intervals of about six inches along the tubes.

12. The assembly of claim 11, wherein the indicia are displayed three times, at each location along the tube, around the circumference of the tube.

13. The assembly of claim 12, wherein the tubes further comprise flow regulator means for restricting the flow of fluids through the tubes.

14. The assembly of claim 13, wherein the separators have at least one groove, the groove being sufficiently wide to accommodate at least one of the tubes, wherein the tubes may be wrapped around the portion of the separator defining the groove.

15. The assembly of claim 13, wherein the separators include slots communicating with the holes, the slots having notched ends.

16. The assembly of claim 13, wherein the tubes include at least one injection portal for injecting fluid into the tubes.

17. An intravascular tube assembly kit, comprising:

(a) at least two substantially clear, plastic intravascular tubes, the tubes bearing a plurality of indicia, the indicia being disposed at substantially constant intervals along the length of the tube, (b) at least two generally flat separators, the separators having spaced-apart holes adapted to receive the tubes through the holes, wherein the separator maintains the spacing of the tubes passing therethrough, and wherein the separator has at least one slot connecting the separator hole with the edge of the separator, whereby one of the tubes may be quickly placed within or removed from the separator hole, (c) adapter means for connecting one end of each of the tubes to different sources of fluid, the adapter means having indicia matching the indicia on the tubes, and (d) cannula connector means for connecting the other end of each of the tubes to a cannula, the cannula connector means having indicia matching the indicia on the tubes.

18. The kit of claim 17, further comprising at least one cannula, adapted for connection to at least one of the tubes.

19. A method of treating a patient in an emergency context, comprising the steps of:

(a) attaching a plurality of sources of therapeutic fluid to a first end of each of a plurality of tubes, each of said tubes having indicia disposed along the length of the tubes, the indicia on each of said tubes being different from the indicia on the others of said tubes, (b) identifying the other end of one of said tubes according to the indicia appearing at the first ends, (c) affixing a cannula to the other end of the identified tube, and (d) injecting one of said therapeutic fluids into the patient, (e) while maintaining the tubes in spaced relation and in an untangled condition through the use of separators.

20. The method of claim 19, further comprising the steps of providing additional fluid for administration to the patient, identifying the correct intravascular tube by observing the indicia on the tubes, and attaching the additional fluid or medication to the correct tube.

21. The method of claim 19, further comprising the step of wrapping excess lengths of tubing around the separator.

* * * * *